United States Patent [19]

Reilly et al.

[11] Patent Number: 5,015,775

[45] Date of Patent: May 14, 1991

[54] ALKYL ARYL SULFONES AND METHOD OF PREPARING THE SAME

[75] Inventors: James L. Reilly, Towamencin; Gordon R. Leader, Tredyffrin Township, Chester County, both of Pa.

[73] Assignee: Atochem North America, Inc., Philadelphia, Pa.

[21] Appl. No.: 175,873

[22] Filed: Mar. 31, 1988

[51] Int. Cl.$^5$ .............................................. C07C 315/00
[52] U.S. Cl. ...................................... 568/28; 568/29; 568/31; 568/33; 568/34; 568/35
[58] Field of Search .................. 568/28, 29, 34, 33, 568/35, 31

[56] References Cited

U.S. PATENT DOCUMENTS

| | | | |
|---|---|---|---|
| 3,125,604 | 3/1964 | Robbins | 568/34 |
| 3,250,812 | 5/1966 | Gilbert | 568/33 |
| 3,501,532 | 3/1970 | Minor et al. | 568/34 |
| 3,579,590 | 5/1971 | Davis | 568/34 |
| 4,386,221 | 5/1983 | Hyatt et al. | 568/28 |

FOREIGN PATENT DOCUMENTS

| | | | |
|---|---|---|---|
| 43-24662 | 10/1968 | Japan | 568/34 |
| 58-206551 | 12/1983 | Japan | 568/34 |

OTHER PUBLICATIONS

M. Grant et al., J. Chem. Soc., p. 2520 (1959).
C. Suter, The Organic Chemistry of Sulfur, pp. 676–677 (1944), John Wiley and Sons, Inc., N.Y.
Organische Schwefel-Verbindungen, p. 1165 (1985), Georg Thieme Verlag Publishers, N.Y.
EPO Search Report for Application No. 89102131.3, corresponding to this U.S. application.
E. E. Gilbert, "A New Synthesis of Methyl Aryl Sulfones", *J. Org. Chem.*, 28:1945 (1963).
J. A. Hyatt et al., "Synthesis of Aryl Alkyl and Aryl Vinyl Sulfones via Friedel-Crafts Reactions of Sulfonyl Fluorides", *Synthesis*, 214–217 (1984).
W. E. Truce et al., "Friedel-Crafts Reactions of Methanesulfonyl Chloride with Benzene and Certain Substituted Benzenes", *J. Amer. Chem. Soc.*, 5032 (1953).
P. Oxley et al., "Amidines. Part II. Preparation of Cyanides, Amides, and Amidines from Carboxylic Acids", *J. Chem. Soc.*, 763–771 (1946).
Suter, C., "Tetracovalent Sulfur Compounds", The *Organic Chemistry of Sulfur*, pp. 673–679 plus References p. 762 (1944).
Premasagar, V. et al., "Methanesulfonic Acid Catalyzed Cyclization of 3-Arylpropanoic and 4-Arylbutanoic Acids to 1-Indanones and 1-Tetralones", *J. Org. Chem.*, pp. 2974–2976, vol. 46, No. 14, 1981.
Eaton, P. et al., "Phosphorus Pentoxide-Methanesulfonic Acid. A Convenient Alternative to Polyphosphoric Acid", *J. Org. Chem.*, vol. 38, No. 23, 1973.
Ueda, M. et al., "A New Synthesis of Diaryl Sulfones", *Synthesis*, pp. 323–325 (Apr. 1984).
Meyer, von Hans, "Zur Kenntnis der Aromatischen Sulfosauren und Sulfone", *Annalen der Chemie*, 433, pp. 327–350 (1923).
Ueda, M. et al., "Synthesis of Aromatic Poly(Ether Ketones)", *Macromolecules*, 20, pp. 2675–2678 (1987).
Bodine, R. et al., "C-Labeled Benzo[a]Pyrene and Derivatives. 1. Efficient Pathways to Labeling the 4,5,11, and 12 Positions", *J. Org. Chem.*, vol. 43, No. 21 (1978).
Kuczynski, H. et al., "O Sulfokwasach Sulfonow Aromatycznych", *Rocznikl Chemll.*, T. XVII, 18, pp. 625–650 (1938), and Chemical Abstract, p. 1940, Col. 3246.
Michael, A. et al., "Zur Kenntniss der Aromatischen Sulfone", pp. 583–587.
Truce, W. et al., "Aromatic Sulonylation", *Sulfones and Sulfoximines*, pp. 532–536, 597.

*Primary Examiner*—Mary E. Ceperley
*Attorney, Agent, or Firm*—Panitch Schwarze Jacobs & Nadel

[57] ABSTRACT

Alkyl aryl sulfones of the formula $R-SO_2-AR-Y_n$, wherein Ar is an aryl compound, Y is a substituent on the aryl compound and R is alkyl or cycloalkyl, and liquid mixtures of positional isomers of the same are prepared by reacting an aryl compound of the formula $Ar-Y_n$, with an alkyl sulfonic acid of the formula $R-SO_3H$ and a phosphorus reagent, preferably under heat. Particularly good yields and pure products are obtained using phosphorus pentoxide. Alkyl aryl sulfones produced by this method are a liquid mixture preferably containing at least two positional isomers, wherein no isomer is present in an amount of more than about 50% of the isomer mixture.

13 Claims, No Drawings

__NUM__5,015,775__NUM__

ALKYL ARYL SULFONES AND METHOD OF PREPARING THE SAME

STATEMENT OF GOVERNMENT INTEREST

This invention was made with Government support under DNA-001-86-C-0176 awarded by the Defense Nuclear Agency. The Government has certain rights in this invention.

FIELD OF THE INVENTION

The present invention relates to the preparation of alkyl aryl sulfones, including an improved method of preparing the same and, more particularly, to liquid mixtures of alkyl aryl sulfones.

BACKGROUND OF THE INVENTION

Liquid alkyl aryl sulfones have proven useful as dielectric media, heat transfer fluids, plasticizers and functional fluids used in hydraulic systems, braking systems, servomechanisms and other devices. The individual isomers of certain alkyl aryl sulfones, however, are solids at room temperature, and are undesirable for fluid applications. Moreover, alkyl aryl sulfones containing impurities often interfere with and impede applications in which such sulfones are used. For example, chlorinated impurities in heat transfer fluids cause corrosion to metal parts in which the fluids are contained and circulated. In addition, condensed aromatic impurities cause limited transparency of the fluid in applications where optical clarity is desirable.

Alkyl aryl sulfones have been prepared by Truce and Vriegen, 75 *J. Amer. Chem. Soc.* 5032 (1953), by reacting alkyl sulfonyl chloride with aromatic hydrocarbons in the presence of aluminum chloride, ferric chloride or other Friedel Crafts catalysts. Typically, however, when alkyl groups are present on an aromatic hydrocarbon, extensive chlorination occurs in the presence of the alkyl sulfonyl chlorides and Friedel Crafts catalysts. For example, a 70% yield of 2,5-dimethylchlorobenzene is obtained from the reaction of p-xylene with methane sulfonyl chloride and aluminum chloride. See Hyatt and White, Synthesis 214-17 (1984).

To avoid side reactions and tar formation, various reagents, such as methane sulfonic anhydride or alkyl sulfonyl fluorides, have been used. See, e.g., Gilbert, 28 *J. Org. Chem.* 1945 (1963); Hyatt and White, *supra*. Alkyl aryl sulfones can also be made by reacting aromatic sulfonic acid salts with alkylating agents, such as methyl iodide or dimethyl sulfate. See, e.g., Oxley, et al., *J. Chem. Soc.* 763 (1946).

These methods have the disadvantage of using expensive chemicals, having long reaction times, failing to work with certain substituted aromatic hydrocarbons, yielding products that are solids or that crystallize over time, or yielding products that are difficult to purify. For example, the method using methane sulfonic anhydrides reacted with orthoxylene generally produces low yields and/or tar formation. Further, the reaction of methane sulfonyl chloride with hydrocarbons, such as toluene and xylene using ferric chloride as a catalyst, typically results in yields below 50% with dark-colored products, even after washing to remove the ferric chloride, and high boiling, chlorinated by-products, difficult to remove from the desired methyl aryl sulfone.

In view of the serious deficiencies and inefficiencies of the prior art, it is desirable to produce liquid mixtures of alkyl aryl sulfones and to have a simple method of preparation that is effective with all aryl positional isomers. While there are a number of methods known in the art for the preparation of diaryl sulfone using phosphorus compounds, see, e.g., U.S. Pat. No. 3,579,590 of Davis; U.S. Pat. No. 3,125,604 of Robbins, none of these methods suggest the preparation of a liquid mixture of positional isomers of alkyl aryl sulfones.

BRIEF SUMMARY OF THE INVENTION

According to the present invention, a liquid mixture of positional isomers of an alkyl aryl sulfone of the formula:

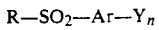

wherein
R is alkyl having 1 to 18 carbon atoms, cycloalkyl having 3 to 10 carbon atoms, halogen-substituted cycloalkyl having 3 to 10 carbon atoms or —XR'-substituted cycloalkyl having 3 to 10 carbon atoms where X is —O—, —S—, —SO—, —CO—, —$SO_2$, —CONR'—, —$SO_2$NR'—, —NR'— or —$CO_2$ and R' is alkyl having 1 to 11 carbon atoms or cycloalkyl having 3 to 11 carbon atoms;

Ar is a homo- or hetero-aromatic mono-, di- or tricyclic moiety, a fused aromatic system containing less than 20 aromatic carbon atoms, or a hetero-aromatic system containing less than 4 hetero atoms selected from the group consisting of O, N, S and P;

Y is a positional substituent on the aryl group and is alkyl having 1 to 12 carbon atoms, cycloalkyl having 3 to 10 carbons, halogen or —XR', wherein X and R, are as defined above; and n is 1 to 10, is produced by reacting an aryl compound of the formula Ar—$Y_n$, with an alkyl sulfonic acid of the formula R—$SO_3$H and a phosphorus reagent wherein Ar, Y, R and n are as defined above, but having at least one free hydrogen on the aryl group.

The reaction is preferably carried out with heating and using a phosphorus reagent selected from the group consisting of phosphorus oxychloride, phosphorus pentachloride, phosphorus pentoxide and polyphosphoric acid, present in an amount at least stoichiometrically equivalent to the alkyl sulfonic acid. Preferably, the reaction results in a liquid mixture containing at least two positional isomers of an alkyl aryl sulfone, wherein no isomer is present in an amount of more than about 50% of the isomer mixture.

DETAILED DESCRIPTION OF PREFERRED EMBODIMENTS

Although the method of preparation of the invention applies to the preparation of alkyl aryl sulfones generally, the method is described and exemplified below with specific examples using simple alkyl sulfonic acids and simple aromatic hydrocarbons. It will be understood by one skilled in the art that analogous reagents can be used to prepare analogous alkyl aryl sulfones. Those skilled in the art will recognize usable reagents other than those exemplified, based upon the present disclosure. Moreover, it will be apparent to one skilled in the art that the method of preparation of this invention readily lends itself to the preparation of other high purity products The reaction of an aryl compound with an alkane sulfonic acid and a phosphorus reagent may be represented by the following equation:

RSO₂OH + Ar—Y<sub>n</sub> + Phosphorus compound
→ RSO₂—Ar—Y<sub>n</sub> + Phosphoric acid by-product wherein R, Ar, Y and n are as previously defined. Examples of phosphorus compounds useful in the invention include one or more of the following: phosphorus oxychloride (a liquid), phosphorus pentachloride (a solid), phosphorus pentoxide (a solid) or polyphosphoric acid (a viscous liquid). Particularly preferred as the phosphorus reagent for catalyzing the above reaction is phosphorus pentoxide.

Examples of aromatic hydrocarbons or mixtures of aromatic hydrocarbons useful in carrying out the present invention include diethyl benzene, halogenated toluene, methyl anisole, cuxmene, cymene and positional isomers of xylenes and chlorobenzenes. In general, the aryl group may be a mono-, di- or tricyclic or fused ring aromatic system having less than 20 carbon atoms in the ring system. The ring system may be an all carbon atom (homo-aromatic) system, or may include up to 3 (less than 4) hetero atoms selected from the group consisting of oxygen, nitrogen, sulfur and phosphorus Particularly preferred aryl groups are the xylenes and toluenes.

The aryl groups are at least monosubstituted and may have up to 10 substituents as indicated by the above formula. Particularly preferred substituents are halogen and lower alkyl groups. The substituents may be on any sterically permissible position of the aryl ring(s).

Alkane sulfonic acids useful in the present invention include methane sulfonic acid, ethane sulfonic acid, cyclohexane sulfonic acid, and other straight chain, branched chain, or mono or polycyclic alkane sulfonic acids. Anhydrous sulfonic acids are preferred and particularly preferred is anhydrous methane sulfonic acid.

The reagents may be added in any order. The preferred addition sequence is aromatic hydrocarbon, alkyl sulfonic acid and then phosphorus compound. In general, the aryl hydrocarbon is added in a stoichiometric excess relative to the alkyl sulfonic acid, and this excess serves as a solvent for the reaction. As will be apparent to those skilled in the art, however, solvents other than aromatic hydrocarbon may be used. In most cases all of the respective reagents may be added at once. With very reactive systems, however, slow addition of the reagents may be desired to prevent a violent exotherm. One skilled in the art may determine the relative reactivity of a given system, based on the particular reagents used.

Generally, the reaction vessel is a flask or analogous container equipped for constant stirring, such as a magnetic stirrer, a reflux condensor to prevent escape of volatile reagents or products, and means for controlling the temperature of the reaction. Preferably, the reaction is carried out with heating at a temperature of about 40° C. to about 220° C. and preferably about 80° C. to 130° C. The temperature of the reaction generally depends upon the reagents' reactivity and volatility. Such temperature be determined by one skilled in the art in view of the particular reagents employed in this process.

The time of reaction varies, dependent upon the reactivity of the reagents, the temperature of the reaction and the percent yield of the product desired. Preferably, the reaction time is about 4 hours for reactions employing higher reaction temperatures and/or relatively more highly reactive reagents to about 28 hours for reactions using highly volatile reagents, relatively low reaction temperatures and/or relatively less reactive reagents.

Gas may evolve during the reaction. For example, when xylene, anhydrous methane sulfonic acid and phosphorus oxychloride are employed as reagents in the method of this invention, hydrogen chloride gas is liberated. As will be apparent to those skilled in the art, such gas may be removed from the reaction vessel by passing a stream of dry, inert gas, such as nitrogen, through the vessel.

When phosphorus oxychloride or phosphorus pentachloride are used to cause the reaction of methane sulfonic acid, or other alkyl sulfonic acids, with an aromatic hydrocarbon, a part of the methane sulfonic acid may be converted to the methane sulfonyl chloride, which can be recovered by distillation or converted to methyl aryl sulfone by a reaction with an aryl hydrocarbon promoted by a Friedel Crafts catalyst. However, the greater portion of the unreacted methane sulfonic acid appears to be combined with the phosphoric acid by-product. This methane sulfonic acid, which is combined with the phosphoric acid by-product, can be converted to methyl aryl sulfone by further heating the by-product phosphoric acid with more of the aromatic hydrocarbon. When phosphorus pentoxide is used as the phosphorus compound, an excess of this reagent (that is, in excess of its stoichiometric equivalent) is used to force the conversion of all of the alkyl sulfonic acid to alkyl aryl sulfone.

The reaction is carried out as described above to yield the desired alkyl aryl sulfone in exceptionally pure form, requiring little further purification with about 30% to about 100% yield. Isolation and purification of the desired product may be carried out using materials and techniques known in the art such as separation funnels, decanting, drying agents, vacuum drying, distillation and fractional distillation, to name a few. The percent yield depends upon the particular reagents used, the temperature of the reaction, the time of the reaction, as well as other factors.

The reaction may be halted when desired, and the product, preferably cooled to room temperature, may be isolated and purified as determined by one skilled in the art. The process of the present invention yields an unusually pure product when compared to previously known methods. The products of this process are relatively free of condensed aromatics and chlorinated by-products (both nuclear and side-chain chlorination), which are often difficult to remove by distillation or crystallization. Because of the purity of the products derived from this process, they are useful in applications where chlorinated or polyaromatic-impurities would interfere, such as heat transfer applications and optical applications, as well as others.

The products of this invention are also useful as dielectrics or functional fluids. In such capacity, it is preferable that the products remain in liquid form. It will be apparent to one skilled in the art that the individual isomers of, for example, methyl xylyl sulfone are all solids at room temperature. However, when none of the positional isomers is present in an amount of more than about 50% of the isomer mixture, the product is a liquid and demonstrates excellent stability.

An example of such a fluid is the isomeric mixture of methyl xylyl sulfones, which is produced when commercial xylene is used as the aromatic hydrocarbon in this process. The boiling point of such a mixture derived from xylene as a reagent in the process of this invention has a high boiling point (about 118° C. to about 130° C. at 0.15 mm), a relatively low viscosity (65 centistokes at 25° C. and 25 centistokes at 37.8° C.), and a low pour point (−18° C.). By using other suitable aromatic hydrocarbons, a mixture of aromatic hydrocarbon isomers or mixtures of totally different aromatic hydrocarbons, a wide variety of useful fluids and solids can be obtained.

The invention will now be illustrated in further detail by reference to the following specific, non-limiting examples

EXAMPLE 1

Xylene (159.2 g, 1.5 moles) was mixed in a flask with anhydrous methane sulfonic acid (48.0 g, 0.5 mole) and phosphorus oxychloride (25.6 g, 0.167 mole) and heated at 130–135° C. for 4 hours while stirring and under reflux. Hydrogen chloride evolved and was swept out as it formed by passing a slow stream of dry nitrogen through the reaction vessel.

After the mixture cooled and stirring was stopped, a heavy lower layer consisting mainly of phosphoric acid separated from the organic phase. The organic phase was removed and 100 ml of water was added to dissolve the lower phase. This solution was then twice extracted with 25 ml amounts of xylene before discarding. The xylene extracts were added to the main organic phase, which was then washed with 100 ml amounts of water, saturated sodium bicarbonate solution and water. The washed organic phase was then dried with anhydrous sodium sulfate and stripped by heating under vacuum to remove unreacted xylene. The light-colored, oily product, an isomeric mixture of methyl xylyl sulfones, weighed 44.1 g. The yield was 43.5% after correcting for small amounts of xylene and MSC (1%) still present. GC analysis showed no presence of detectable high boilers or chloroxylenes.

EXAMPLE 2

A 45% yield of final purified product mixture (methyl xylyl sulfones) was obtained following the procedure in Example 1, but using 1,2-xylene instead of the commercial xylene mixture. The method described in Example 1 also gave about 40–45% yields of purified product when 1:1 mixtures of para and ortho, and para and meta xylene isomers were used instead of the commercial xylene mixture.

EXAMPLE 3

Toluene (92.06 g, 1.0 mole) was reacted with anhydrous methane sulfonic acid (48.05 g, 0.5 mole) and phosphorus oxychloride (25.5 g, 0.17 mole) at reflux temperature for 4 hours. After work-up of the product as in Example 1 28.2 g of crude product was obtained. The yield was 35.1% after correction for the small amounts of MSC and toluene still present. GC analyses of product showed no chloro compounds present.

EXAMPLE 4

Anisole (2.16.3 g, 2.0 moles) was mixed in a flask with anhydrous methane sulfonic acid (64.8 g, 1.0 mole) and phosphorus oxychloride (54.1 g, 0.56 mole) and was heated while stirring at 120–125° C. for 5 hours. A nitrogen purge was used to sweep out HCl gas as it formed. Subsequent treatment of the reaction mixture after cooling was the same as in Example 1. The washed and dried product solution was then heated in a distillation unit with a fractionating column to remove unreacted anisole. Products remaining in the distillation unit were finally diluted with N-butanol and crystallized from this solvent. A yield of 35% of methyl p-methoxyphenyl sulfone was obtained.

EXAMPLE 5

Xylene (159.2 g, 1.5 moles) was mixed in a flask with anhydrous methane sulfonic acid (48 grams, 0.50 mole) and phosphorus pentachloride (23 grams, 0.11 mole) and was heated at 130° C. for 4 hours while stirring and under reflux. Subsequent treatment of the reaction mixture after cooling was the same as in Example 1. The final washed and stripped crude product weighed 30.9 g, a 33% yield, and its composition was the same in all respects as that of the product made in Example 1.

EXAMPLE 6

A 49% yield of the final product mixture (methyl xylyl sulfone) was obtained following the procedure in Example 5, but using phosphorus pentoxide (23.7 g, 0.17 mole) instead of phosphorus pentachloride. Composition of the final washed and stripped crude product was the same in all respects as that of the product made in Example 1.

EXAMPLE 7

A 73% yield of the final product mixture (methyl xylyl sulfone) was obtained following the procedure in Example 5, but using phosphorus pentoxide (48.26 g, 0.34 mole) and a reflux time of 12 hours. Composition of the final washed and stripped crude product was the same in all respects as that of the product made in Example 1.

EXAMPLE 8

Chlorobenzene (168.8 g, 1.50 mole) was reacted with anhydrous methane sulfonic acid (65.52 g, 0.68 mole) and phosphorus pentoxide (48.3 g, 0.34 mole) under reflux at 135° C. for 5 hours. The reaction mixture was cooled to room temperature. 100 ml of water was added dropwise. This mixture was stirred for 10 minutes and then the organic phase was diluted with 150 ml of chloroform. The water layer was discarded and organic phase was washed with 2 100 ml portions of water. The chloroform and excess chlorobenzene were stripped under vacuum yielding 62 g (48% yield) of a mixture of isomers of methyl chlorophenyl sulfone.

EXAMPLE 9

Fluorobenzene (144.2 g, 1.5 moles) was reacted with anhydrous methane sulfonic acid (48.0 g, 0.5 mole) and phosphorus pentoxide (23.66 g, 0.17 mole) under reflux at 85° C. for 28 hours. After work-up of the reaction mixture as in Example 7, 5 g (3%) of a mixture of isomers of methyl fluorophenyl sulfone was obtained.

EXAMPLE 10

Xylene (159.2 g, 1.5 moles), anhydrous ethane sulfonic acid (55.07 g, 0.50 mole) and phosphorus pentoxide (48.26 g, 0.34 mole) were heated at 110° C. with stirring for 12 hours. The reaction mixture was cooled to room temperature and then 100 ml of water was added dropwise. This mixture was stirred for 10 minutes. The organic phase was separated and washed twice with 100 ml portions of water as in Example 8. The excess xylene was then stripped under vacuum yielding a mixture of isomers of ethyl xylyl sulfone.

EXAMPLE 12

Xylene (159.2 g, 1.5 moles), anhydrous cyclohexane sulfonic acid (74.5 g, 0.25 mole) and phosphorus pentoxide (48.26 g, 0.34 mole) were heated at 110° C. with stirring for 12 hours. This reaction mixture was then worked up as in Example 11, yielding a mixture of isomers of cyclohexyl xylyl sulfone.

EXAMPLE 13

An isomeric mixture of diethyl benzene (268.44 g, 2.0 moles), anhydrous methane sulfonic acid (96.1 g, 1.0 mole) and phosphorus oxychloride (25.6 g, 2.17 moles) were heated at 90° C. with stirring for 8 hours. Treatment of the reaction mixture after cooling was the same as in Example 1 and 25 g (12% yield) of methyl diethylphenyl sulfone was obtained.

The present invention may be embodied in other specific forms without departing from the spirit or central attributes thereof and, accordingly, reference should be made to the appended claims, rather than the specification, as indicating the scope of the invention.

We claim:

1. A process of making an alkyl aryl sulfone of the formula:

$$R-SO_2-Ar-Y_n$$

wherein

R is alkyl having 1 to 18 carbon atoms, cycloalkyl having 3 to 10 carbon atoms, halogen-substituted cycloalkyl having 3 to 10 carbon atoms —XR'-substituted cycloalkyl having 3 to 10 carbon atoms where X is —O—, —S—, —SO—, —CO—, —SO$_2$—, —CONR'—, —SO$_2$NR'—, —NR'— or —CO$_2$— and R' is alkyl having 1 to 11 carbon atoms, or cycloalkyl having 3 to 11 carbon atoms;

Ar is an aromatic mono-, di-, tricyclic moiety or a fused aromatic system containing 6 to 20 aromatic carbon atoms, or a hetero-aromatic system containing 4 to 20 aromatic carbon atoms and 1 to 3 hetero atoms wherein said hetero atoms in the aromatic ring are selected from the group consisting of O, N, S and P;

Y is a substituent on the aryl group and is alkyl having 1 to 12 carbon atoms, cycloalkyl having 3 to 10 carbons, halogen, or —XR', wherein X and R' are as defined above; and n is 1 to 10, which comprises reacting an aryl compound of the formula Ar—Y$_n$ with alkyl sulfonic acid of the formula R—SO$_3$H and a phosphorus reagent wherein Ar, Y, R and n are as defined above, but having at least one free hydrogen on the aryl group.

2. The process according to claim 1, wherein the reaction is carried out with heating at a temperature of about 40° C. to about 220° C.

3. The process according to claim 2, wherein the reaction temperature is about 80° C. to about 130° C.

4. The process according to claim 1, wherein the phosphorus reagent is selected from the group consisting of phosphorus oxychloride, phosphorus pentachloride, phosphorus pentoxide, and polyphosphoric acid.

5. The process according to claim 1, wherein the phosphorus reagent is present in an amount at least stoichiometrically equivalent to the alkyl sulfonic acid.

6. The process according to claim 1, wherein the reagent is phosphorus oxychloride.

7. The process according to claim 1, wherein the reagent is phosphorus pentoxide.

8. The process according to claim 7, wherein the phosphorus pentoxide is present in an amount greater than a stoichiometric equivalent to the alkyl sulfonic acid.

9. The process according to claim 1, wherein the aryl compound is xylene.

10. The process according to claim 1, wherein the aryl compound is toluene.

11. The process according to claim 1, wherein the aryl compound is anisole.

12. The process according to claim 1, wherein the aryl compound is chlorobenzene.

13. The process according to claim 1, wherein xylene is reacted with anhydrous methane sulfonic acid and phosphorus pentoxide to form a liquid mixture of positional isomers of methyl xylyl sulfone.

* * * * *